(12) United States Patent
Skinner

(10) Patent No.: US 6,629,841 B1
(45) Date of Patent: Oct. 7, 2003

(54) ADJUSTABLE DENTAL IMPRESSION TRAY AND METHODS FOR USING SAME

(76) Inventor: Gregory C. Skinner, 250 S. Lyon Ave., Suite B, Hemet, CA (US) 92543

( * ) Notice: Subject to any disclaimer, the term of this patent is extended or adjusted under 35 U.S.C. 154(b) by 0 days.

(21) Appl. No.: 09/649,198

(22) Filed: Aug. 28, 2000

(51) Int. Cl.[7] .............................................. A61C 9/00
(52) U.S. Cl. ...................................................... 433/43
(58) Field of Search ........................... 433/41, 43, 214, 433/42, 45, 44, 37

(56) References Cited

U.S. PATENT DOCUMENTS

| | | | | |
|---|---|---|---|---|
| 2,594,832 A | * | 4/1952 | Wentzel ......................... | 433/41 |
| 2,685,137 A | * | 8/1954 | Thompson ..................... | 433/41 |
| 2,860,414 A | * | 11/1958 | Brant ............................ | 433/43 |
| 3,574,259 A | * | 4/1971 | Jones ............................ | 433/43 |
| 3,987,548 A | * | 10/1976 | Jones ............................ | 433/43 |
| 4,145,812 A | | 3/1979 | Johnson et al. ................ | 32/17 |
| 4,432,728 A | * | 2/1984 | Skarky ......................... | 433/37 |
| 4,763,791 A | | 8/1988 | Halverson et al. .......... | 206/570 |
| 5,040,976 A | | 8/1991 | Ubel, III et al. .............. | 433/41 |
| 5,064,371 A | | 11/1991 | Smeltzer ....................... | 433/37 |
| 5,076,785 A | | 12/1991 | Tsai .............................. | 433/46 |
| 5,297,960 A | | 3/1994 | Burns ........................... | 433/41 |
| 5,336,086 A | | 8/1994 | Simmen et al. ................ | 433/37 |
| 5,340,308 A | | 8/1994 | Cukjati .......................... | 433/41 |
| 5,503,497 A | | 4/1996 | Dudley et al. ............... | 403/103 |
| 5,513,985 A | | 5/1996 | Robertson ..................... | 433/38 |
| 5,580,244 A | | 12/1996 | White ........................... | 433/37 |
| 5,582,488 A | | 12/1996 | Dudley et al. ............... | 403/103 |
| 5,636,985 A | | 6/1997 | Simmen et al. ................ | 433/37 |
| 5,733,118 A | | 3/1998 | Pankuch et al. ............... | 433/38 |
| 6,071,121 A | * | 6/2000 | Simon ........................... | 433/37 |
| 6,428,315 B1 | * | 8/2002 | Prestipino et al. ............. | 433/45 |

FOREIGN PATENT DOCUMENTS

| | | | | |
|---|---|---|---|---|
| FR | 737739 | * | 12/1932 | ................... 433/43 |
| IT | 417420 | * | 1/1947 | ................... 433/43 |

* cited by examiner

Primary Examiner—Todd E. Manahan
(74) Attorney, Agent, or Firm—Pate Pierce & Baird

(57) ABSTRACT

An adjustable dental impression tray includes a first and second arcuate member movably attached at a proximal end of each arcuate member. The adjustable dental impression tray includes a handle to facilitate removal of the tray from a person's mouth. The dental impression tray also includes an adjustment mechanism which allows the user to position the first arcuate member relative to the second arcuate member to form a U-shaped channel which approximates the patients dentition. The dental impression is further configured with a locking member to receive and retain impression material into the tray.

33 Claims, 7 Drawing Sheets

ADJUSTABLE DENTAL IMPRESSION TRAY AND METHODS FOR USING SAME

BACKGROUND

1. Field of the Invention

This invention relates to dental implements, and more particularly, to novel dental impression trays that are mechanically adjustable to accommodate various mouth sizes in order to obtain an accurate impression of the upper and/or lower dentition of a patient.

2. The Background Art

With regards to dentistry, an impression is often used to create an imprint or negative likeness of the teeth and adjacent portions of the jaw (e.g., tooth formations, the contour of the gums, etc.) preparatory to dental repair, orthodontics and restoration of missing dental structures. Impressions are typically made by placing a soft, semi-fluid material within the confines of an open trough or channel of an arcuate tray which is then positioned within the mouth of a patient, thus allowing the material to set or cure. Depending upon the material used, the set impression may be either hard or have some elastic characteristics.

To provide the most accurate articulation, the impression cast should generally represent the entire dental arch. In this regard, the impression cast can be used to establish interproximal contacts, buccal and lingual contours and occlusion with the opposing teeth. From the negative or female cast of the teeth and surrounding structures, a positive reproduction or male cast may be created for the purpose of fabricating inlays, crowns, bridge retainers, dentures, restorations or the like.

Traditionally, before an impression cast of the dentition is created, a stock tray is selected by the dentist or dental assistant that will generally fit the dental arch of the particular patient. Since the dental arch may differ widely from patient to patient, various sizes of impression trays (e.g., small, medium and large) were developed by those skilled in the art to accommodate various mouth sizes, bite radii of teeth and to correspond to upper and lower anterior or quadrant impression sites.

For example, those skilled in the art developed prior art dental impression trays formed of metal, such as stainless steel, and having a pair of spaced-apart vertical walls joined by a semi-rigid mesh material disposed horizontally between the opposing vertical walls. Extending outwardly in structural relation to at least a portion of the surface facing of one of the vertical walls, a handle member may be provided to facilitate a means for gripping the impression tray for purposes of manual manipulation. In addition, an open trough or channel is generally formed between the opposing vertical walls, wherein the horizontally disposed mesh material provides a porous surface flooring for the trough. In operation, the mesh material provides a means for permitting excess flow of impression material to become displaced and extruded there through. Dental impression trays of the prior art may further include openings formed in the vertical walls of the trough or channel which generally function as an anchoring surface for the impression, thus allowing the excess flow of impression material to become attached thereto.

Although seemingly useful for their intended purposes, there are several practical disadvantages of prior art dental impression trays comprised of metal. For example, a significant disadvantage of prior art metal impression trays includes the difficulty associated with maintaining proper cleaning and sanitation of the impression trays using heat or chemical sterilization methods or techniques to avoid cross-contamination in order to be able to reuse the various sized stock metal impression trays from patient to patient.

Attempting to alleviate some of the disadvantages associated with the amount of time and energy expended to maintain proper sanitation of prior art metal impression trays, in addition to the costs associated therewith, disposable impression trays were developed by those skilled in the art. As noted above, since the dental arch may differ widely from patient to patient, various sizes of disposable impression trays (e.g., small, medium, and large) were developed to accommodate various mouth sizes, bite radii of teeth, and to correspond to upper and lower anterior or quadrant impression sites.

In accordance with other such prior art apparatus and techniques for making an impression cast of the upper and/or lower dentition of a patient, those skilled in the art developed adjustable impression trays. For example, an adjustable impression tray of the prior art may comprise a primary impression unit and a movable extension unit telescopically mounted on the primary unit for adjustable relative thereto. The primary unit being provided with primary leg portions having secondary leg portions extending therefrom, wherein the primary leg portions include a first flap means extending outwardly therefrom and over the secondary leg portions. In operation, the secondary leg portions comprise a tab means cooperative with the first flap means of the primary leg portions so as to facilitate the first flap means being movable relative to the tab means. The movable extension unit further comprising a second flap means having a series of slots therein for registry with the tab means of the secondary leg portions for fixation in relation to the primary leg portions of the impression tray.

Another example of prior art adjustable impression trays includes a main arcuate portion with parallel spaced vertical walls having extension portions slidably disposed in frictional engagement therewith for lengthwise adjustment in relation to the main arcuate portion. The engagement means between the extension portions and the main arcuate portion of the impression tray may include T-shaped rails formed in the outer faces of the opposing walls and corresponding recesses formed in the inner faces of the respective walls of the extension portions. Similarly, annular recesses may be formed in the outer faces of the opposing walls and corresponding annular nibs may be formed in the inner faces of the respective walls of the extension portions to provide a slidable engagement there between.

A meaningful disadvantage with prior art adjustable impression trays of the general type disclosed herein is that they only provide means for accommodating a structural adjustment in the dimensional length of the channel. In this regard, because these prior art adjustable impression trays fail to provide for any adjustment in the dimensional width associated with various sizes of the dental arch, they are generally limited in their particular utilization.

In an effort to accommodate an adjustment in the dimensional width of a dental impression tray, those skilled in the art developed heat-expansive impression trays which may be formed of a thermoplastic material which is malleable at elevated temperatures so that the impression tray can be generally shaped and configured in such a manner so as to accommodate the corresponding dental arch of a particular patient. For example, prior art heat-expansive impression trays may structurally comprise an elongated channel including a buccal side, a lingual side, and an occlusal side. The occlusal side of the channel including an outwardly extending folded section which may be fully or partially unfolded when the channel is heated, thereby providing a means for expanding the dimensional width of the elongated channel. Two additional folded sections formed in opposed posterior portions of the impression tray may also be provided which, when heated at a specific softening temperature, can be partially or fully unfolded by pulling the posterior ends of the tray away from the anterior portion of the same, thus extending the dimensional length of the elongated channel.

While prior art adjustable and heat-expansive impression trays may appear generally suitable for their intended purposes, these prior art impression trays nevertheless leave much to be desired from the standpoint of effectiveness of operation, manufacturing costs, simplicity of construction in relation to a multiplicity of parts, and functionality as to universal application. As will be appreciated in this particular art, economic considerations are significant when dealing with the highly competitive dental industry, since multiple stock impression trays (e.g., small, medium, and large) or complicated devices are frequently found to be commercially impractical. Accordingly, even a slight savings in cost may substantially enhance the commercial appeal of a particular component or assembly when considering issues of mass production of the product.

In accordance therewith, it would be desirable to provide an adjustable dental impression tray which realizes the advantages of the prior art devices while at the same time eliminates the disadvantages associated therewith. Such an adjustable dental impression tray is disclosed and claimed herein.

BRIEF SUMMARY AND OBJECTS OF THE INVENTION

In view of the foregoing, it is a primary object of the present invention to provide novel dental impression trays which may be mechanically adjusted to accommodate various mouth sizes, bite radii of teeth, and to correspond to upper, lower, anterior, quadrant, or triple bite impression sites.

It is also an object of the present invention to provide an adjustable dental impression tray which is formed of a disposable material, thus avoiding the disadvantages associated with having to clean and sanitize metal impression trays.

It is further an object of the present invention to provide an adjustable dental impression tray which may be adjusted to the specific size of the patient's mouth, thereby eliminating the need for a dentist to stock various sizes of impression trays (e.g., small, medium, and large) in order to accommodate different dental arch configurations.

Additionally, it is an object of the present invention to provide an adjustable dental impression tray which increases the accuracy of the impression cast, while decreasing dental chair time.

Similarly, it is an object of the present invention to provide an adjustable dental impression tray which reduces the possibility of deformation of the impression cast.

It is a further object of the present invention to provide an adjustable dental impression tray which simple in construction, effective in operation, and inexpensive to manufacture.

Consistent with the foregoing objects, and in accordance with the invention as embodied and broadly described herein, an adjustable dental impression tray includes a first arcuate member having a distal end and a proximal end. A second arcuate member having a distal end and a proximal end is preferably movable connected to the first arcuate member adjacent the proximal end of each arcuate member. Each arcuate member is adapted to receive a quantity of impression material. A handle may be attached to one of the arcuate members to facilitate easy removal of the dental impression tray with minimal deformation of the impression material.

The dental impression tray of the present invention preferably includes an adjustment mechanism for selectively fixing the position of the first arcuate member relative to the second arcuate member. The adjustment mechanism may include the first arcuate member having an opening, and a second arcuate member having a fastener member corresponding to the opening in the first arcuate member. In one presently preferred embodiment, the fastener member includes a post configured within the proximal end of the first arcuate member with the opening positioned within the proximal end of the second arcuate member. The post and opening may be configured for movable mating engagement with each other, thereby permitting the first and second arcuate members to be selectively positioned relative to each other. In another presently preferred embodiment, the adjustment mechanism includes concentric gears with a spring-loaded button device for releasing the gears and allowing the arcuate membersto move relative to each other. When the button is disengaged, the concentric gears realign preventing further movement. Thus, the dental impression tray of the present invention is pivotally adjustable through a range of motion allowing one tray to closely and comfortably fit a wide variety of dentition sizes.

The first and second arcuate walls include an outer wall. In one presently preferred embodiment, the first and second arcuate members each include a frame member attached to and spread apart from the outer wall. A membrane may extend between the frame member and a centerline portion of the outer wall of each arcuate member, along the length of the outer wall, thus providing a surface upon which the impression material may be placed. Thus, an upper and lower tray portion are simultaneously created within the adjustable dental tray which allows a mold to be taken of the upper and lower dentition simultaneously. This "triple bite" configuration allows the user to not only create an impression of the upper and lower dentition, but allows the user to create a mold which shows the bite relationship between the two.

The first and second arcuate members are configured such that a portion of the first arcuate member can be positioned to closely overlap a portion of the second arcuated member, forming an overlap portion. The first and second arcuate members may be configured such that the first and second arcuate members can be positioned relative to each other to form a substantially U-shaped channel between the outer walls of the first and second arcuate members and a perimeter of the overlap portion. This channel approximates the curvature of a person's dentition.

In another presently preferred embodiment, the first and second arcuate members each include an inner wall spaced apart from the outer wall which, together with the membrane extending there between, form a generally U-shaped channel approximating the curvature of a person's dentition.

The outer wall of at least one of the arcuate members may include a notch adjacent the proximal end of the arcuate member which permits the user to break arcuate member at the notch. This notch allows the user to create a "quadrant" dental tray for taking an impression of the upper or lower left or right portions of the patient's dentition, by breaking off the appropriate arcuate member at the notch. The outer wall of the arcuate members may also include a notch positioned adjacent a middle portion of each arcuate member between the distal and proximal ends. This notch allows the user to break the arcuate members to create an "anterior" dental tray for taking a dental impression of the front portion of the patient's upper or lower dentition.

In another presently preferred embodiment, at lease one of the arcuate members includes a locking member for retaining the impression material. The locking member may include a flange member which extends along a portion of one of the arcuate members. In another presently preferred embodiment, the locking member may include vents configured within at least one of the arcuate members which allows a portion of the impression material to flow through the vents and anchor itself to arcuate member.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DESCRIPTIONS OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 7, is not intended to limit the scope of the invention, as claimed, but it is merely representative of the presently preferred embodiments of the invention. The presently preferred embodiments of the invention will be best understood by reference to the drawings, wherein like parts are designated by like numerals throughout.

Figure 1:
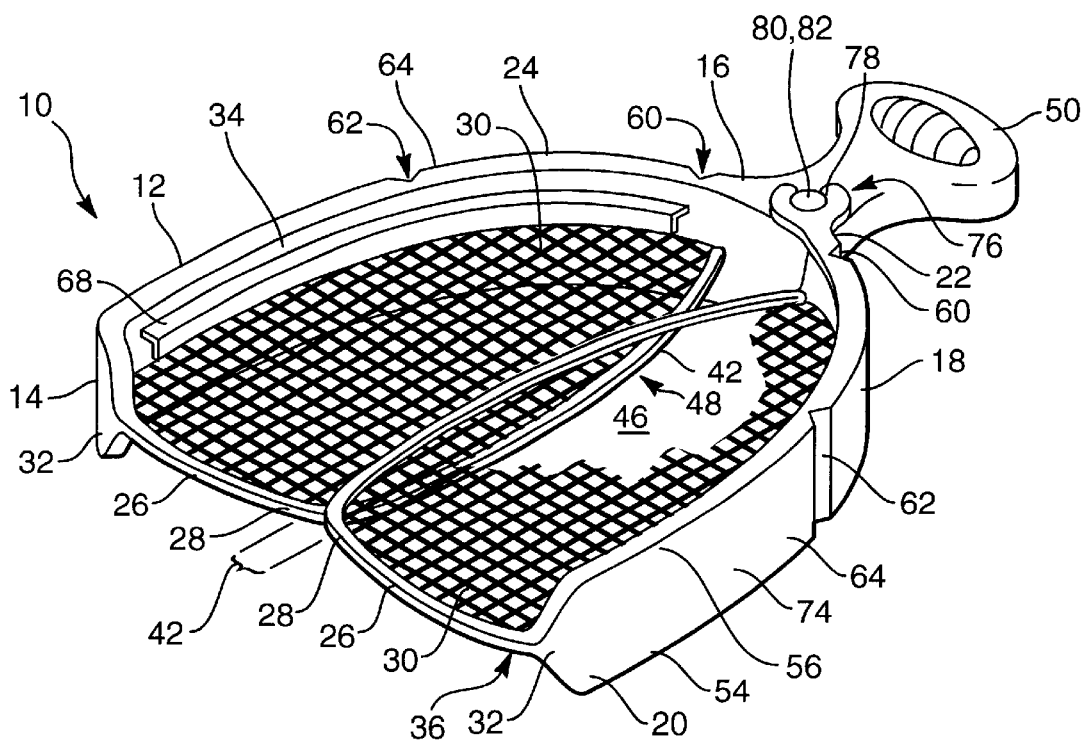
FIG. 1 is a perspective view of one presently preferred embodiment of an adjustable dental impression tray.

One presently preferred embodiment of the present invention, designated generally at 10, is best illustrated in FIG. 1. As shown, an adjustable dental impression tray 10 includes a first arcuate member 12 having a distal end 14 and a proximal end 16. A second arcuate member 18 having a distal end 20 and a proximal end 22 is preferably movably connected to the first arcuate member 12 adjacent the proximal end 18, 24 of each arcuate member 12, 18. The first and second arcuate members 12, 18 each include an outer wall 24. In one presently preferred embodiment, the first and second arcuate members 12, 18 each include a frame member 26 attached to the outer wall 24. A portion 28 of the frame member 26 is spaced apart from the outer wall 24 of each of the arcuate members 12, 18. A membrane 30 may extend between the frame member 26 and the outer wall 24 of each arcuate member 12, 18 along the length of the outer wall 24. In this configuration, the arcuate members 12, 18 are suitable for holding impression material.

Figure 2:
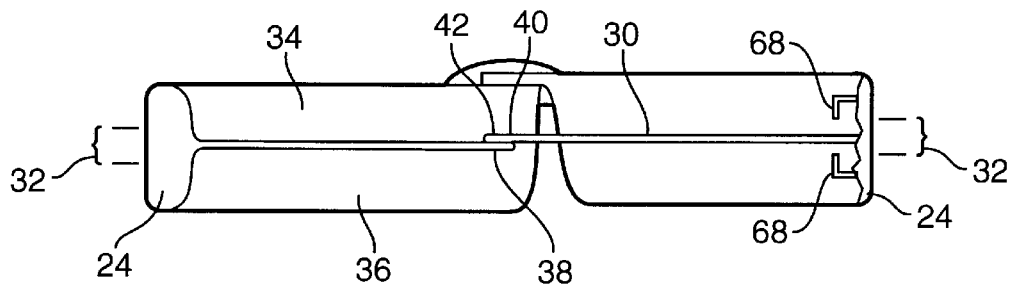
FIG. 2 is a front plan view of the embodiment of FIG. 1 in a partially closed position.

With reference now to FIGS. 1 and 2, the membrane 30 in one embodiment of the present invention extends from a centerline portion 32 of the outer wall 24, preferably along the length of the outer wall 24. It will be appreciated by those of skill in the art that with the membrane 30 extending from the centerline portion 32 of the outer wall 24 an upper 34 and lower 36 tray portion of the adjustable dental tray 10 are simultaneously created. It will further by appreciated by those of skill in the art that this creates a "triple bite" or "multiple impression" tray known in the art to allow a mold to be taken of the upper and lower dentition simultaneously to more accurately determine the relative positions of the upper and lower teeth during a bite. The upper impression corresponds to an impression section of maxilla, the lower impression corresponds to a complimentary section of mandible and the two complimentary impressions jointly provide an impression of the bite relationship of mandible to maxilla.

One suitable material for a membrane 30 is a fabric made form nonwoven spun-bonded filaments. It will be appreciated by those of skill in the art that the weight to area ratio of the membrane extending between the outer wall 24 and the frame member 26, and the air permeability between the upper 34 and lower 36 tray portions can be predetermined for maximum advantage. In one embodiment, the weight to area ratio is less than 0.4 ounces per sheet yard as the membrane extends between the outer wall 24 and the frame member 26. The air permeability, in one presently preferred embodiment, may be greater than about 110 cubic feet per minute per square foot as measured according to ASTM-D.737–75 standards. Other examples of membrane 30 materials include, perforated or continuous sheets of silicone-based film, foil or other highly malleable metal, either continuous or perforated, ceramics, plastics, rubbers, or other metals or metal alloys.

It will further be appreciated that various methods of attachment of the membrane could be utilized to practice the teachings of this invention. It will further be appreciated by those of skill in the art that the membrane 30 may extend from a base portion 54 or top portion 56 to create a single upper or lower tray. In one presently preferred embodiment, the membrane 30 is integral with, and preferably formed of the same material, as the arcuate members 12, 18.

The first and second arcuate members 12, 18 are configured such that a portion 38 of the first arcuate member 12 can be positioned to closely overlap a portion 40 of the second arcuate member 18, forming an overlap portion 42. The first and second arcuate members 12, 18 may be configured such that the first and second arcuate members 12, 18 can be positioned relative to each other to form a substantially U-shaped channel 46 between the outer walls 24 of the first and second arcuate members 12, 18 and a perimeter 48 of the overlap portion 42. It will be appreciated by those of skill in the art that this channel 46 can approximate the curvature of a person's dentition. Accordingly, each arcuate member 12, 18 is adapted to receive a quantity of impression material (not shown).

In a presently preferred embodiment, a handle 50 is attached to at least one of the arcuate members 12, 18. The handle 50 helps facilitate removal of the dental impression tray 10 without deforming the impression material within the tray 10. In the embodiment illustrated in FIGS. 1 through 4b and 7, the handle 50 is attached to and integral with the first arcuate member 12. It will be appreciated by those of skill in the art that there are various ways to configure a handle 50 or means to facilitate removal of the dental impression tray 10. Some alternative forms include tabs, grips, or flange members attached at various positions along the arcuate members 12, 18.

With reference again to FIGS. 1 and 2, at least one of the arcuate members 12, 18 includes a locking member 64 for retaining the impression material. In a presently preferred embodiment, the locking member 64 includes an L-shaped flange member 66 which extends from the inside of the outer wall 24 along the length of each of the arcuate members 12, 18 on opposite sides of the membrane 30. It will be appreciated by those of skill in the art that where the membrane 30 extends from either the base portion 54 or the top portion 56 of the outer wall 26, the L-shaped locking member 66 is needed on only an interior of channel 46 of the dental impression tray 10.

With specific reference to FIG. 2, one arm 68 of the L-shaped flange on each side of the membrane 30 extends towards the membrane 30. In this configuration, impression material will fill into a groove 70 created by the L-shaped flange 66 when a patient bites down on the adjustable dental impression tray 10 as a dental mold is created. Those with skill in the art will appreciate that the L-shape flange 66 will secure the impression material to the adjustable dental impression tray 10 as it is removed from a patient's mouth.

In another presently preferred embodiment, the locking member 64 may include vents 272 (see FIG. 7) configured within at least one of the arcuate members 12, 18 which allows a portion of the impression material (not shown) to flow through the vents 272 and anchor itself to the arcuate member 12, 18. It will be appreciated by those of skill in the art that the teachings of this invention may be practiced using a variety of locking member 64 configurations.

Figure 3:
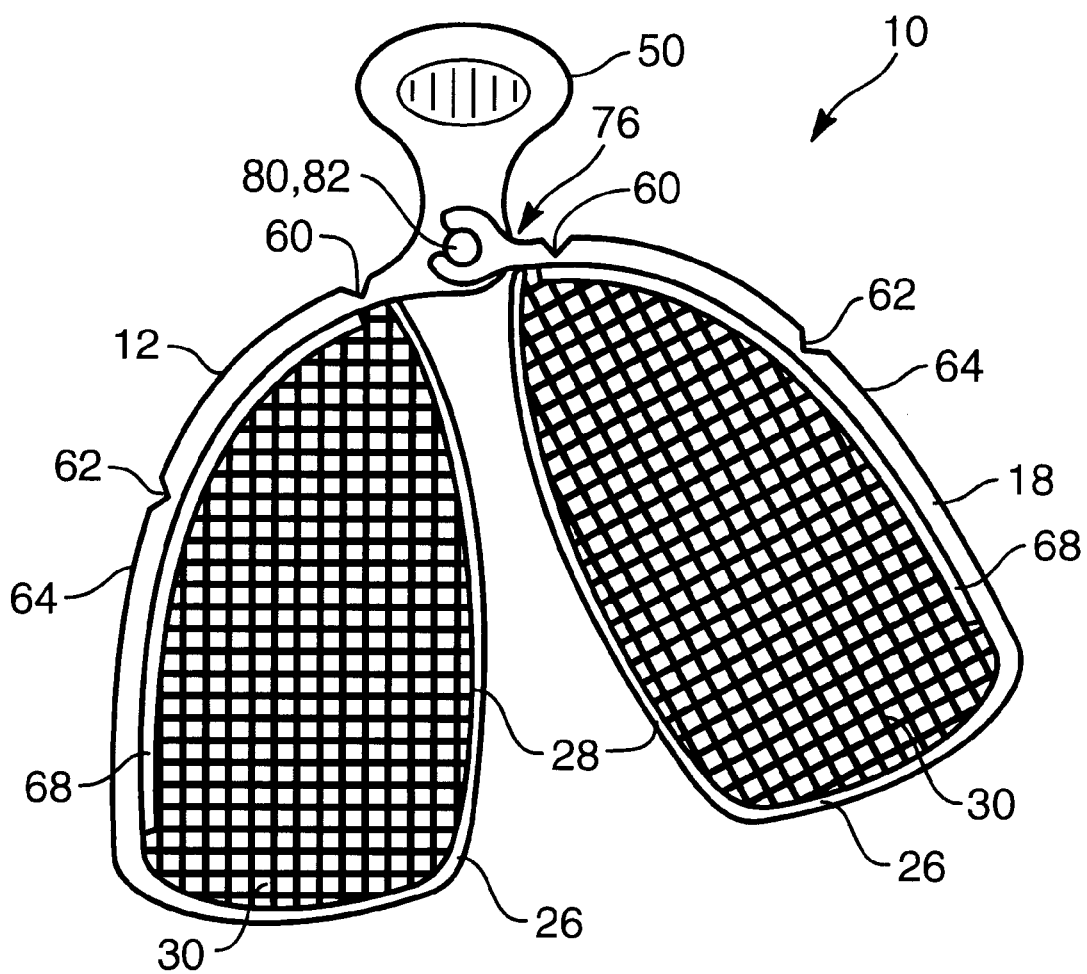
FIG. 3 is a top plan view of the embodiment of FIG. 1 with a first and second arcuate member adjusted into an open position.
Figure 4A:
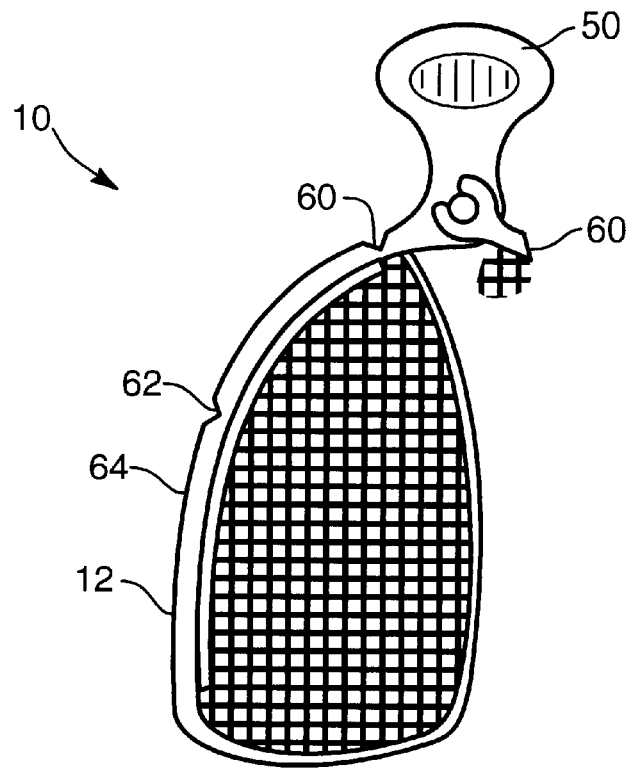
FIG. 4a is a top plan view of the embodiment of FIG. 1 showing an arcuate member broken away to form a quadrant tray.
Figure 4B:
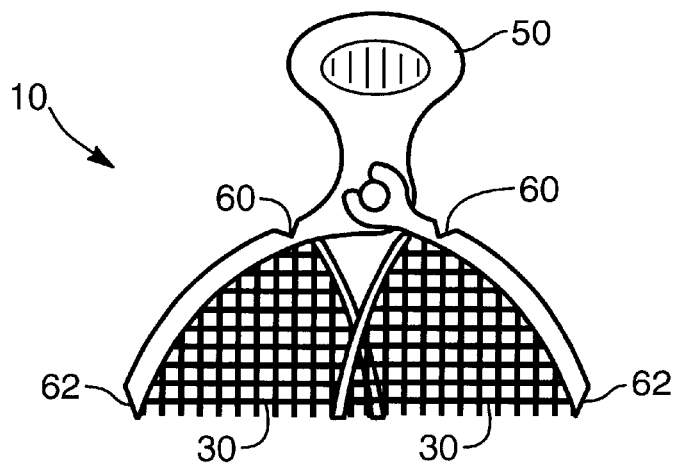
FIG. 4b is a top plan view of the embodiment of FIG. 1 showing an both arcuate members partially broken away to form an anterior tray.

Referring now to FIGS. 3, 4a and 4b, the outer wall 24 of at least one of the arcuate members 12, 18 may include a proximal notch 60 adjacent the proximal ends 16, 22 of each arcuate member 12, 18 which permits the user to break arcuate member 12, 18 at the proximal notch 60. It will be appreciated by those of skill in the art that this allows the user to create a "quadrant" dental tray for taking an impression of the left or right portions of the patient's upper or lower dentition. The outer wall 24 of the arcuate members 12, 18 may also include a medial notch 62 positioned adjacent a middle portion 63 of the arcuate members 12, 18 between the distal 14, 20 and proximal ends 16, 22, which permits the user to break the arcuate members 12, 18 at these notches 62. It will be appreciated by those of skill in the art that this will allow the user to create an "anterior" dental tray for taking a dental impression of the front portion of the patient's upper or lower dentition. It will be further appreciated by those of skill in the art that the first and second arcuate members 12, 18, must be of sufficient rigidity to allow a user to break the arcuate members 12, 18 at the notches 60, 62. It will be appreciated that the depth of the notches 60, 62 may vary depending on the material used to create the arcuate members 12, 18. Additionally, it will be appreciated by those of skill in the art that there are numerous ways to allow the user to break the arcuate members 12, 18 to form a quadrant or anterior tray, which fall within the teachings of this invention.

Figure 5:
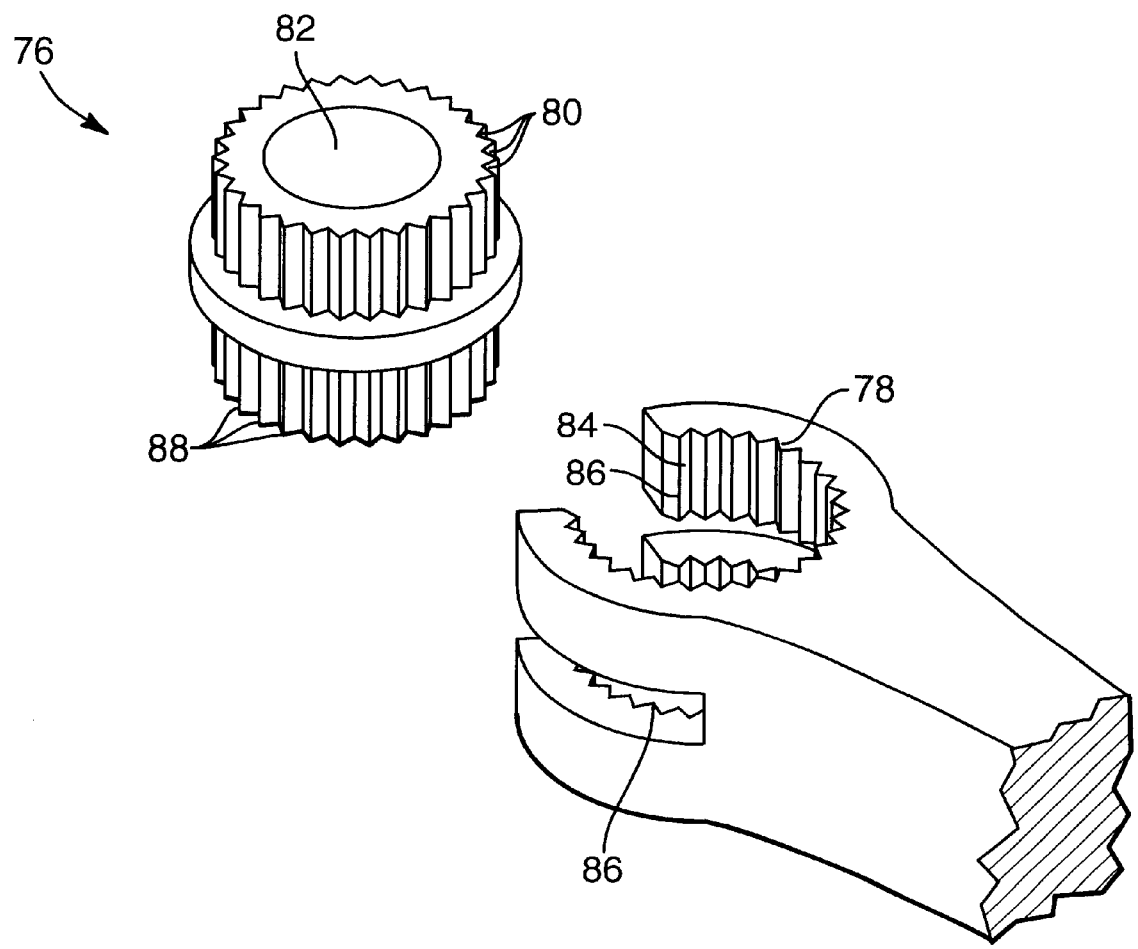
FIG. 5 is a perspective exploded view of the embodiment of FIG. 1 showing an adjustment mechanism.

Referring now to FIG. 5, the dental impression tray 10 of the present invention preferably includes an adjustment mechanism 76 for selectively fixing the position of the first arcuate member 12 relative to the second arcuate member 18. In one preferred embodiment, the adjustment mechanism 76 includes an opening 78 configured within the proximal end 22 of the second arcuate member 18 and a fastener member 80, corresponding to the opening 78, configured within the proximal end 16 first arcuate member 12. In once presently preferred embodiment, the fastener member 80 includes a post 82 configured within the proximal end 16 of the first arcuate member 12, with the opening 78 generally configured in the shape of a C. An interior surface 84 of the opening 78 is configured with teeth members 86. The post 82 is configured with corresponding teeth 88 such that the opening 78 and post 82 may be positioned in movable mating engaged with each other. A first prong 90 and second prong 92 of the C-shaped opening 78 are flexible, thereby allowing the user to apply a force to the second arcuate member 18 such that the first prong 90 and second prong 92 spread apart allowing the second arcuate member 18 to rotate about the post 82 of the first arcuate member 12. In this configuration, the first and second arcuate members 12, 18 may be selectively positioned relative to each other. It will be appreciated by those of skill in the art that the first and second prongs 90, 92 should be of such rigidity that when the adjustable dental impression tray is not be adjusted, the C-shaped opening 78 returns to mating engagement with the post 82, holding the first and second arcuate member 12, 18 in a fixed position relative to each other. The configuration of the opening 78 will thus be based in part upon the material of the arcuate member.

Other adjustment mechanisms may included various fastener means attached to the first and second arcuate members 12, 18 including "ball cap" fasteners, ratchet strap fasteners, or other types of fasteners.

Figure 6:
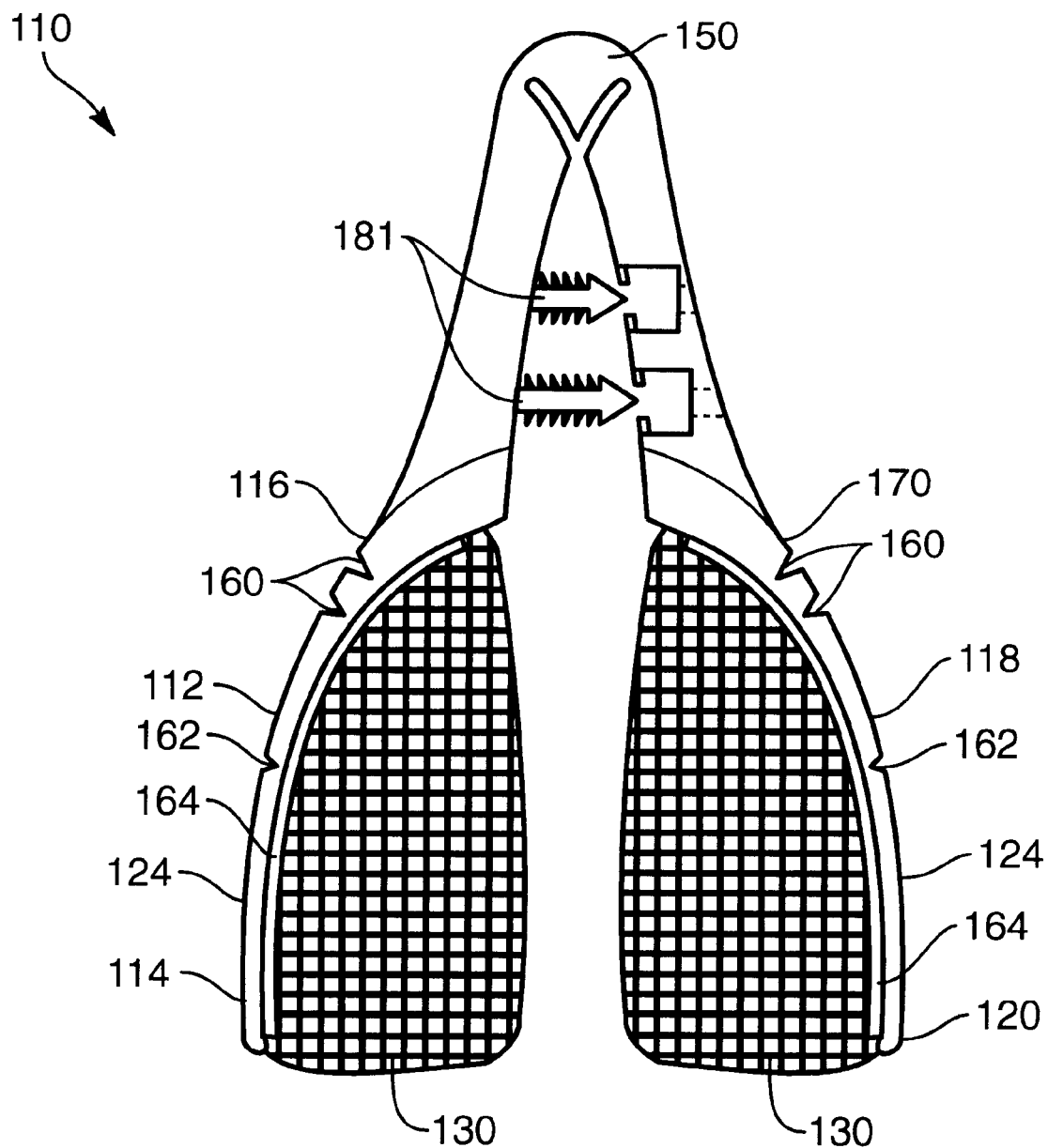
FIG. 6 is a top plan view of yet another embodiment of the present invention illustrating an alternative adjustment mechanism.

Turning now to FIG. 6, an alternative embodiment of the adjustable dental impression tray is generally designated at 110. In this embodiment, a first arcuate member 112, having a distal end 114 and a proximal end 116, is connected to and integral with a second arcuate member 118 having a distal end 120 and a proximal end 122, at the proximal ends 116, 122 of the arcuate members 112, 118. As with previously described embodiments, a membrane 130 may extend from an outer wall 124 of each arcuate member 112, 118 along the length of the outer wall 124. The membrane 130 in this embodiment extends from a centerline portion (not shown) of the outer wall 24, but could also extend from a base or top portion (not shown).

As in earlier embodiments, the first and second arcuate members 112, 118 are configured to overlap and form a substantially U-shaped channel which approximates the curvature of a persons' dentition. Accordingly, each arcuate member 112, 118 is adapted to receive a quantity if impression material (not shown). A handle 150 portion is configured adjacent the proximal ends 116, 122 of each arcuate member 112, 118. As in embodiment described above, each arcuate member 112, 118 may include a locking member 164 for retaining the impression material. The embodiment of FIG. 6 may also include proximal notches 160 adjacent the proximal ends 116, 122 of the arcuate members 112, 118 and medial notches 162 positioned adjacent middle portions 163 of the arcuate members 112, 118 between the distal 114, 120 and proximal ends 116, 122 of the arcuate members 112, 118. These notches allow the user to break the adjustable dental impression tray at the appropriate place to create a "quadrant" or "anterior" dental tray known in the art for taking an impression of the left or right portions of the patient's upper or lower dentition, or the front portion of the patient's upper or lower dentition, respectively.

The embodiment illustrated in FIG. 6 includes an adjustment mechanism 176. The adjustment mechanism 176 includes at least one and preferably two ratchet strips 181 attached to the first arcuate member 112. At least one and preferably two openings 178 are configured within the second arcuate member 118 opposite the ratchet strips 181. The opening includes a neck portion 179 configured to receive and retain the ratchet strips 181, thus allowing the dental tray to be adjusted to a variety of positions. It will be appreciated by those of skill in the art that other embodiments may have as adjustment mechanisms a wire which is of sufficient rigidity to hold the first and second arcuate members 112, 118 in a fixed position relative to each other and yet malleable enough to reposition the first and second arcuate members 112, 118 relative to each other.

Figure 7:
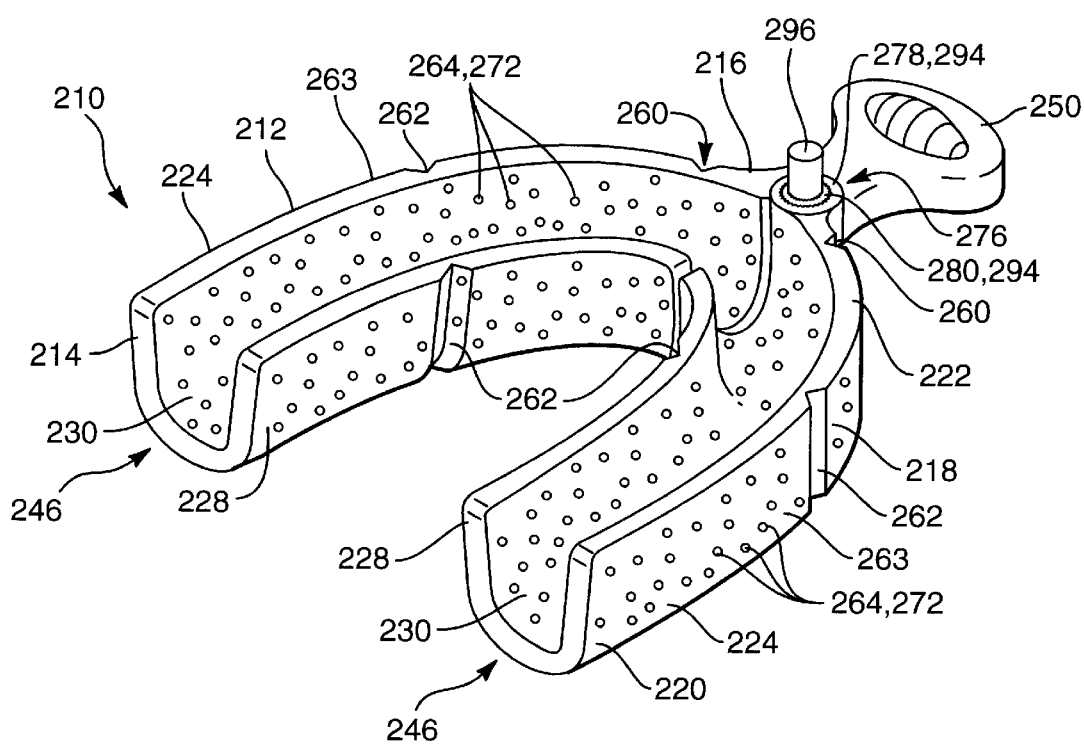
FIG. 7 is a perspective view of a another embodiment of the present invention illustrating arcuate members with inner and outer walls.

Referring now to FIG. 7, another alternative embodiment of the present invention is generally designated at 210. In this embodiment, a first arcuate member 212, having a distal end 214 and a proximal end 216, is connected to a second arcuate member 218 having a distal end 220 and a proximal end 222. The first and second arcuate members 212, 218 each include an inner wall 228 spaced apart from an outer wall 224. A membrane 230 may extend between the inner wall 228 and the outer wall 224 thus forming a generally U-shaped channel 246 approximating the curvature of a person's dentition. In the presently preferred embodiment of FIG. 7, the inner wall 228, outer wall 224, and membrane, are integral with each other.

In the presently preferred embodiment illustrated in FIG. 7, a handle 250 is attached to at least one of the arcuate members 212, 218. As described in earlier embodiments, the handle 250 is attached to and integral with the first arcuate member 212. As also described above, at least one of the arcuate members 212, 218 and preferably each arcuate member 212, 218 includes a locking member 264 for retaining impression material. In the presently preferred embodiment of FIG. 7, the locking member 264 includes vents 272 configured within at least one and preferably each of the arcuate members 212, 218. The vents 272 allow a portion of the impression material to flow through and anchor itself to the arcuate members 212, 218.

In the preferred embodiment of FIG. 7, the outer wall 224 and inner wall 228 of each arcuate members 212, 218 may include a proximal notch 260 adjacent the proximal ends 216, 222 of the arcuate members 212, 218 which permits the user to break arcuate member 212, 218 at the proximal notch 260. The outer wall 224 and inner wall 228 of the arcuate members 212, 218 may also include a medial notch 262 positioned adjacent a middle portion 263 of the arcuate members 212, 218 between the distal 214, 220 and proximal ends 216, 222, which permits the user to break the arcuate members 212, 218 at these notches 262. It will be appreciated by those of skill in the art that the notches allow the user to create a "quadrant" dental tray for taking an impression of the left or right portions of the patient's upper or lower dentition or an "anterior" dental tray for taking a dental impression of the front portion of the patient's upper or lower dentition.

he dental impression tray 210 of the present invention illustrated in FIG. 7 preferably includes an adjustment mechanism 276 for selectively fixing the position of the first arcuate member 212 relative to the second arcuate member 218. The adjustment mechanism 276 includes an opening 278 configured within the proximal end 222 of the second arcuate member 218 and a fastener member 280, corresponding to the opening 278, configured within the proximal end 216 first arcuate member 212. The fastener member 280 includes a first gear 294 configured within the proximal end 216 of the first arcuate member 212. The opening 278 is also configured in gear formation about the first gear 294 to form concentric gears. A spring-loaded button 296, which when depressed, allows the concentric gears 294 to disengage allowing the first and second arcuate members 212, 218 to rotate or move relative to each other. When the button 296 is released, the concentric gears 294 realign holding the position of the first arcuate member 212 fixed relative to the second arcuate member 218.

Figure 8:
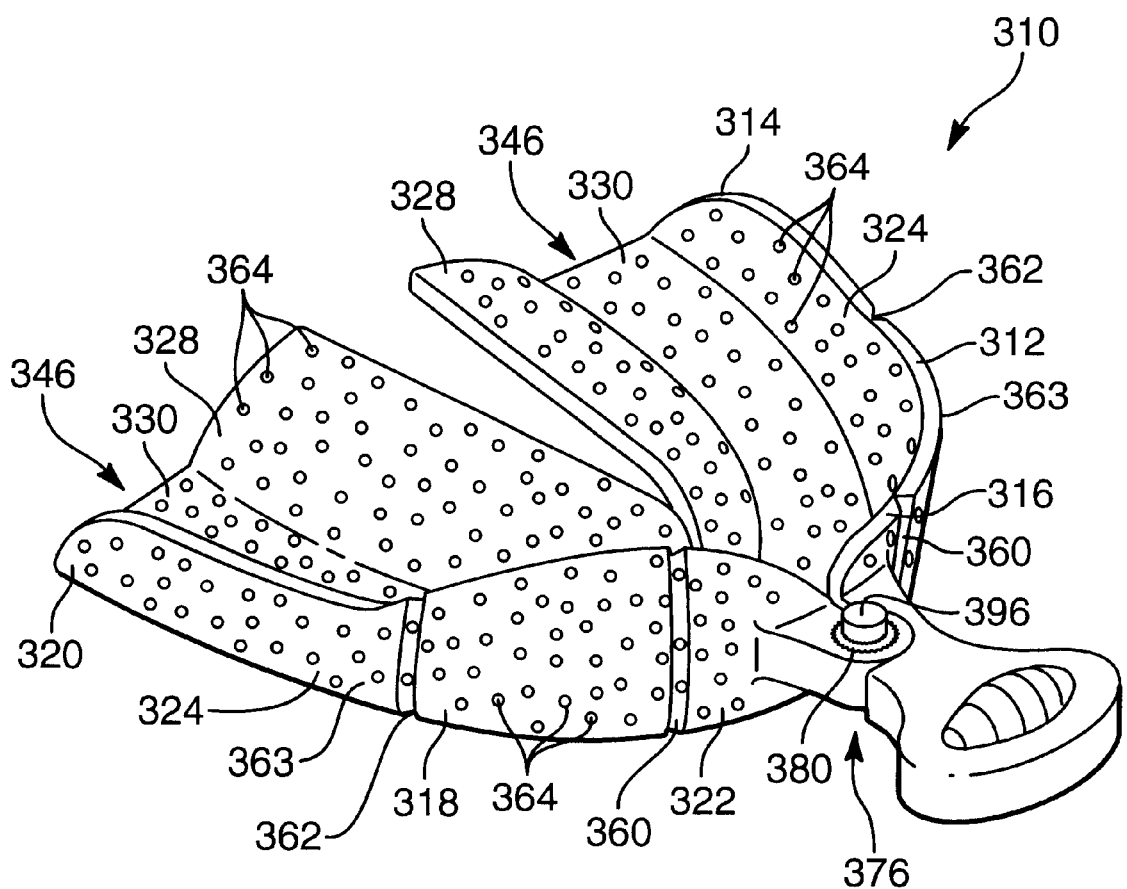
FIG. 8 is a perspective view of a another embodiment of the present invention illustrating an upper tray with a plate support.

Referring now to FIG. 8, another alternative embodiment of the present invention is generally designated at 310. In this embodiment, a first arcuate member 312, having a distal end 314 and a proximal end 316, is connected to a second arcuate member 318 having a distal end 320 and a proximal end 322. As with previous embodiments, the first and second arcuate members 312, 318 each include and inner wall 328 spaced apart from an outer wall 324 with a membrane 330 extending between the inner wall 328 and the outer wall 324 forming a generally U-shaped channel 346 approximating the curvature of a person's dentition. It will be appreciated by those of skill in the art that the embodiment illustrated in FIG. 8 may be used as an upper partial edentulous tray. The teachings of this invention may also be practiced on a variety of dental trays including, full edentulous, triple byte, denture, various other impression trays, and the like.

The tray 310 illustrated in FIG. 8 may include a handle 350 attached to one of the arcuate members 312, 318 and a locking member 364 for retaining impression material.

In the preferred embodiment of FIG. 8, the outer wall 324 and inner wall 328 of each arcuate members 312, 318 may include a proximal notch 360 adjacent the proximal ends 316, 322 of the arcuate members 312, 318 and a medial notch 362 positioned adjacent a middle portion 363 or the arcuate member 312, 318 between the distal 314, 320 and proximal ends 316, 322. These permit the user to break the arcuate members 312, 318 to create a "quadrant" dental tray or an "anterior" dental tray.

The dental impression tray 310 of the present invention illustrated in FIG. 8 preferably includes an adjustment mechanism 376 for selectively fixing the position of the first arcuate member 312 relative to the second arcuate member 318. The adjustment mechanism 376 includes an post member 396 and a fastener member 380, configured to matingly engage the post member 396. In this embodiment, the first and second arcuate members 312, 318 are positioned relative to each other and permanently snapped together to approximate the dentition of the patient. It will be appreciated by those of skill in the art that any number of snap members may be utilized to fixed the first arcuate member 312 to preselected position relative to the second arcuate member 318.

Referring again to FIGS. 1 through 5, the arcuate members 12, 18 of the presently preferred embodiment are each injection molded using molded plastic, and specifically, high density polyethylene. It will be appreciated by those of skill in the art, however, that the arcuate members 12, 18 may be formed of a variety of other sufficiently sturdy materials such as, metal alloys, fiberglass, ceramics, graphite, any of numerous organic, synthetic or processed materials, including thermoplastic or thermosetting polymers of high molecular weight with or without additives, such as, plasticisers, auto oxidants, extenders, colorants, ultraviolet light stabilizers, or fillers and/or other composite material which are capable of being sterilized by conventional autoclave or chemical methods or processes. It will further be appreciated by those of skill in the art that the teachings of this invention may be practiced to create various styles of adjustable trays, including, upper and lower edentulous trays, upper and lower partial edentulous trays, upper and lower full trays, triple bite trays, and other types of impression trays.

The adjustable dental impression tray 10 of the present invention is used by approximating a patient's dentition and selectively positioning the first arcuate member 12 relative to the second arcuate member 18 to form a generally U-shaped channel 46 which approximates the dentition. After comparing the approximation to the actual dentition and refining the position of the arcuate members 12, 18 relative to each other, impression material may be applied into the channel 46. The dental impression tray 10 is inserted into the patient's mouth and onto the patient's dentition. After allowing the impression material to at least partially set, the dental impression tray 10 is removed from patient's mouth. After utilizing the resulting mold for its intended purpose, the dental impression tray may be discarded. In an embodiment where the first and second arcuate members 12, 18 each comprise an outer wall 24 having a proximal notch 60 adjacent a proximal end 22 of each arcuate member 12, 18, or a medial notch 62 the user approximates a patient's dentition and selectively positions the first arcuate member 12 relative to the second arcuate member 18 such that a generally U-shaped channel 46 approximates the dentition. The user may then determine which portion of a patient's dentition to create a mold for a break off one of either the first or second arcuate member 12, 18 at the appropriate notch 60, 62 to create a "quadrant" tray or an "anterior" tray. The impression material is then applied into the remaining channel 46 of the dental impression tray 10. The dental impression tray 10 is placed into the patient's mouth and onto the patient's dentition. After allowing the impression material to at least partially set, the dental impression tray 10 is removed from the patient's mouth.

From the above discussion, it will be appreciated that the present invention provides novel adjustable dental impression trays and methods for using the same. In particular, the present invention provides an adjustable dental impression tray which may be adjusted to accommodate various mouth sizes, bite radii of teeth, and to correspond to upper and/or lower, anterior or quadrant impression sites.

Unlike prior art devices, the present invention provides an adjustable dental impression tray comprising an adjustment assembly which may be manually adjusted to the specific size of the patient's mouth (e.g., small, medium, or large), thereby eliminating the need for a dentist to inventory various conventional sizes of stock impression trays. Additionally, the present invention may be formed of a disposable material, thus avoiding the disadvantages associated with having to clean and sanitize metal impression trays.

Consistent with the foregoing, the present invention provides an adjustable dental impression tray which increases the accuracy of the impression cast, while decreasing dental chair time for the patient. Similarly, the present invention reduces the possibility of deformation of the impression cast, is simple in construction, effective in operation, and inexpensive to manufacture.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An adjustable dental impression tray, comprising:
    a first arcuate member having an outer wall and an opening, wherein said outer wall comprises at least one notch formed along a length thereof;
    a second arcuate member configured to selectively engage said first arcuate member, said second arcuate member having an outer wall, wherein said outer wall comprises at least one notch formed along a length thereof;
    a fastener member monolithically formed as part of the second arcuate member;
    said arcuate members forming a channel adapted to receive a quantity of impression material; and
    an adjustment mechanism for selectively adjusting said first arcuate member in at least one fixed position relative to said second arcuate member, wherein said fastener member of said second arcuate member is configured to selectively engage said opening of said first arcuate member to provide adjustable securement of the first arcuate member relative to the second arcuate member to define a width of said dental impression tray.

2. The adjustable dental impression tray as defined in claim 1, wherein each of said first and second arcuate member further comprise a frame member attached to said outer wall, at least a portion of said frame member being spaced apart from the outer wall of each of the respective first and second arcuate members and wherein a membrane extends between the frame member and the outer wall of each of the arcuate members.

3. The adjustable dental impression tray as defined in claim 2, wherein said membrane is attached substantially along a length of said outer wall of said first and second arcuate members adjacent a centerline portion of said outer walls.

4. The adjustable dental impression tray as defined in claim 2, wherein said membrane is attached substantially along a length of said outer wall of said first and second acuate members adjacent a base portion of the outer walls.

5. The adjustable dental impression tray as defined in claim 2, wherein said outer wall of each respective arcuate member is monolithically formed with said membrane of each respective arcuate member.

6. The adjustable dental impression tray as defined in claim 2, wherein said first and second acuate members are configured such that a portion of said first arcuate member can be positioned to overlap a portion of said second arcuate member, thereby forming an overlap portion.

7. The adjustable dental impression tray as defined in claim 1, wherein said channel comprises a substantially U-shaped configuration approximating a curvature of the dentition of a patient.

8. The adjustable dental impression tray as defined in claim 1, wherein said first and second arcuate members each comprise an inner wall spaced apart from said outer wall.

9. The adjustable dental impression tray as defined in claim 1, wherein said outer wall of at least one of said first and second arcuate members comprises a second notch formed along a length of said arcuate member between a distal end and a proximal end thereof.

10. The adjustable dental impression tray as defined in claim 1, wherein said fastener member comprises a post configured to selectively engage said opening.

11. The adjustable dental impression tray as defined in claim 1, wherein the first arcuate member comprises a proximal end and the second arcuate member comprises a proximal end monolithically formed with said proximal end of the first arcuate member.

12. The adjustable dental impression tray as defined in claim 1, wherein at least one of said first and second arcuate members comprises a locking member for retaining said impression material.

13. The adjustable dental impression tray as defined in claim 12, wherein said locking member comprises a flange member extending along at least a portion of a length of said arcuate members.

14. The adjustable dental impression tray as defined in claim 12, wherein said locking member comprises a plurality of receiving apertures configured within at least one of said first and second arcuate members, said receiving apertures having a dimensional periphery sufficient to allow a portion of said impression material to flow through.

15. The adjustable dental impression tray as defined in claim 1, wherein one of said arcuate member comprises a handle.

16. The adjustable dental impression tray as defined in claim 7, wherein said first and second arcuate members are made of plastic.

17. An adjustable dental impression tray, comprising:
   a first arcuate member having an outer wall and an opening, wherein said outer wall comprises at least one notch along a length thereof;
   a second arcuate member configured to selectively engage said first arcuate member, said second arcuate member having an outer wall, wherein said outer wall comprises at least one notch formed along a length thereof;
   a fastener member monolithically formed as part of the second arcuate member;
   said arcuate members forming a channel adapted to receive a quantity of impression material;
   an adjustment mechanism for selectively adjusting said first arcuate member in at least one fixed position relative to said second arcuate member, wherein said fastener member of the second arcuate member is configured to selectively engage said opening of the first arcuate member to provide adjustable securement of the first arcuate member relative to the second arcuate member to define a width of said dental impression tray; and
   a handle monolithically formed with said first arcuate member.

18. The adjustable dental impression tray as defined in claim 17, further comprising a locking member formed in relation to said first and second arcuate members for retaining said impression material.

19. The adjustable dental impression tray as defined in claim 18, wherein said locking member comprises a flange member extending along at least a portion of a length of said arcuate members.

20. The adjustable dental impression tray as defined in claim 18, wherein said locking member comprises a plurality of receiving apertures configured within at least one of said first and second arcuate members, said receiving apertures having a dimensional periphery sufficient to allow a portion of said impression material to flow through.

21. The adjustable dental impression tray as defined in claim 17, wherein said outer wall of at least one of said first and second arcuate members comprises a second notch formed along a length of said arcuate member between a distal end and a proximal end thereof.

22. The adjustable dental impression tray as defined in claim 17, wherein each of said first and second arcuate members further comprise a frame member attached to said outer wall, at least a portion of said frame member being spaced apart from the outer wall of each of the respective first and second arcuate members and wherein a membrane extends between the frame member and the outer wall of each of the arcuate members.

23. The adjustable dental impression tray as defined in claim 22, wherein said members is attached substantially along a length of said outer wall of said first and second arcuate members adjacent a centerline portion of said outer walls.

24. The adjustable dental impression tray as defined in claim 22, wherein said membrane is attached substantially along a length of said outer wall of each of said first and second arcuate members at a base of the outer wall.

25. The adjustable dental impression tray as defined in claim 22, wherein said outer wall of each respective arcuate member is monolithically formed with said membrane of each respective arcuate member.

26. The adjustable dental impression tray as defined in claim 17, wherein said first and second arcuate members each comprise an inner wall spaced apart from said outer wall.

27. The adjustable dental impression tray as defined in claim 17, wherein said channel comprises a substantially U-shaped configuration approximating a curvature of the dentition of a patient.

28. The adjustable dental impression tray as defined in claim 17, wherein said fastener member comprises a post configured to selectively engage said opening.

29. The adjustable dental impression tray as defined in claim 17, wherein the first arcuate member comprises a proximal end and the second arcuate member comprises a proximal end monolithically formed with said proximal end of the first arcuate member.

30. The adjustable dental impression tray as defined in claim 17, wherein said first and second arcuate members are made of plastic.

31. A method of using an adjustable dental impression tray, said method comprising the steps of:
   selecting a dental impression tray having a first arcuate member and a second arcuate member, said second arcuate member having an opening selectively engaging a post monolithically formed as part of said first arcuate member to form a channel for receiving impression material;
   approximating a dentition;
   selectively adjusting said first arcuate member relative to the second acuate member such that said channel approximates said dentition; selectively adjusting a length of at least one of said arcuate members;

introducing an amount of said impression material into said channel;

positioning said channel in relation to said dentition;

allowing said impression material to at least partially set; and removing said impression tray from engagement with said dentition.

32. The method as defined in claim 31, wherein each of said first and second arcuate members comprise an outer wall having at least one notch formed in a length thereof.

33. The method as defined in claim 32, further comprising the step of breaking off at least one of said notches formed in said first and second arcuate members to form a partial dental impression tray.

* * * * *

UNITED STATES PATENT AND TRADEMARK OFFICE
CERTIFICATE OF CORRECTION

PATENT NO. : 6,629,841 B1
DATED : October 7, 2003
INVENTOR(S) : Skinner

It is certified that error appears in the above-identified patent and that said Letters Patent is hereby corrected as shown below:

Column 3,
Line 63, after "which", insert -- is --.

Column 4,
Line 28, please delete "membersto", and insert therefore -- members to --.
Line 67, after "break", please insert -- the --.

Column 5,
Lines 51 and 54, please delete "a another", and insert therefore -- another --.

Column 10,
Line 43, please delete "byte", and insert therefore -- bite --.

Column 13,
Line 41, please delete "7", and insert therefore -- 1 --.

Column 14,
Line 26, please delete "members", and insert therefore -- membrane --.

Column 15,
Line 1, after "dentition;", please insert a line break and begin a new subparagraph before selectively --.

Signed and Sealed this

Twenty-fourth Day of August, 2004

JON W. DUDAS
*Director of the United States Patent and Trademark Office*